(12) United States Patent
Alqahtani et al.

(10) Patent No.: US 12,310,731 B2
(45) Date of Patent: May 27, 2025

(54) METHOD AND SYSTEM FOR DETERMINING AND MONITORING RELATIVE CONSCIOUSNESS OF A SUBJECT

(71) Applicant: NAJRAN UNIVERSITY, Najran (SA)

(72) Inventors: Ali Saeed Alqahtani, Najran (SA); Saeed Saad Alahmari, Najran (SA)

(73) Assignee: NAJRAN UNIVERSITY, Najran (SA)

( * ) Notice: Subject to any disclaimer, the term of this patent is extended or adjusted under 35 U.S.C. 154(b) by 85 days.

(21) Appl. No.: 18/319,211

(22) Filed: May 17, 2023

(65) Prior Publication Data

US 2024/0382124 A1 Nov. 21, 2024

(51) Int. Cl.
  *A61B 5/16* (2006.01)
  *A61B 5/00* (2006.01)
  *A61B 5/11* (2006.01)

(52) U.S. Cl.
  CPC ............ *A61B 5/163* (2017.08); *A61B 5/1124* (2013.01); *A61B 5/746* (2013.01)

(58) Field of Classification Search
  CPC ........ A61B 5/163; A61B 5/1124; A61B 5/746
  See application file for complete search history.

(56) References Cited

U.S. PATENT DOCUMENTS

| | | | |
|---|---|---|---|
| 6,416,480 B1 | 7/2002 | Nenov | |
| 11,298,021 B2 * | 4/2022 | Muhsin | A61B 5/022 |
| 11,504,051 B2 * | 11/2022 | Krueger | A61B 5/163 |
| 12,076,136 B2 * | 9/2024 | Tran | A61B 5/14532 |
| 2012/0161969 A1 | 6/2012 | Husen et al. | |
| 2017/0360334 A1 * | 12/2017 | Oksala | A61B 5/0205 |

FOREIGN PATENT DOCUMENTS

| | | |
|---|---|---|
| IN | 202211029038 | 5/2022 |
| KR | 10-2014-0101968 | 8/2014 |

OTHER PUBLICATIONS

Alanazi et al. ; A Critical Review for an Accurate and Dynamic Predication for the Outcomes of Traumatic Brain Injury based on Glasgow Outcome Scale ; J. Med. Sci., 13(4) ; May 15, 2013 ; 10 Pages.

* cited by examiner

*Primary Examiner* — John A Tweel, Jr.
(74) *Attorney, Agent, or Firm* — Oblon, McClelland, Maier & Neustadt, L.L.P.

(57) ABSTRACT

A method, system, and device for monitoring the relative consciousness of a subject includes conducting response tests, by a consciousness detection system, on the subject to obtain a plurality of response test results. The response test includes an eye movement test conducted with a camera sensor, and the plurality of response test results are analyzed by comparison to a machine learning module to quantify the eye movement of the subject. The consciousness detection system includes a controller, the camera sensor and an alarm. The controller includes a processor to calculate a consciousness score and a memory. The method includes recording the response test results in the memory, analyzing, with the circuitry of the processor, the response test results to determine a consciousness score, triggering an alarm based on the consciousness score indicating a loss of consciousness, and repeating the response test at predetermined regularly timed intervals.

15 Claims, 9 Drawing Sheets

METHOD AND SYSTEM FOR DETERMINING AND MONITORING RELATIVE CONSCIOUSNESS OF A SUBJECT

BACKGROUND

Technical Field

The present disclosure is directed to medical device technology and methods for patient care. The present disclosure is more particularly directed to devices and methods for monitoring the relative consciousness of a subject.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Brain traumatic injuries' (BMI) patients require intensive care from healthcare providers. One of the most substantial tasks for physicians in BMI cases, is the periodic evaluation of patient consciousness levels. Nurses often monitor the consciousness level of patients according to the Glasgow Coma Scale. The Glasgow Coma Scale (GCS) is a clinical scale that is used to reliably measure a person's level of consciousness after a brain injury. The GCS includes three parameters: eye movement, motor response and verbal response. These parameters have various score ranges associated with them which indicate the patient's level of response. The levels of response in the parameters of the GCS are measured and rated with scores from 1—for no response, up to normal values of 4 (for Eye-movement), 5 (for Verbal response), and 6 (for Motor response). The scores from each parameter are added to obtain a value that is referred to as a total consciousness score (TCS). Thus, the TCS has values between three and fifteen, three being a worst-case score and fifteen being the highest score. Monitoring BMI patients is labor-intensive and time-consuming. BMI patients can suddenly transition to a comatose state from a conscious state at any moment during their stay at the hospital for a variety of reasons. Often nurses may not notice the transition in a timely manner or misdiagnose the transition as deep sleep. If the transition is not noticed and/or if treatment to improve the patient's condition is not performed in a timely manner, the patient's TCS may continue to fall, sometimes resulting in death. Treatment to improve TCS scores may be time-consuming and expensive. Timely identification and early medical intervention can help patients to maintain stability and recover faster.

Accordingly, it is an object of the present disclosure to provide a system and method which can automatically and accurately monitor the relative consciousness of a subject.

SUMMARY

In an exemplary embodiment, a method for monitoring the relative consciousness of a subject is described. The relative consciousness of an individual may refer to the individual's score on a medical consciousness evaluation scale such as the Glasgow Coma Scale, or the individual's evaluated binary state of consciousness or unconsciousness at one time when compared to an evaluation at another time. The method includes conducting at least one response test on the subject to obtain a plurality of response test results. The response test may include an eye movement test conducted with a camera sensor and the plurality of response test results are analyzed by comparison to a machine learning module to quantify the eye movement of the subject. The response test is administered by a consciousness detection system. The consciousness detection system includes a controller, a camera sensor, and an alarm. The controller includes a processor having circuitry programed to calculate a consciousness score, and a memory. The method includes recording the response test results in the memory of the processor. The method also includes analyzing, with the circuitry of the processor, the response test results to determine a consciousness score. In addition, the method includes triggering an alarm based on a consciousness score which is indicative of a loss of consciousness. The method further includes repeating the at least one response test at predetermined regularly timed intervals. The repetition is initiated by the processor.

In an exemplary embodiment, a device for monitoring the relative consciousness of a subject is described. The device includes at least one sensor of a consciousness detection system, a monitor, an input unit, and a network module. The consciousness detection system includes a controller, at least one sensor, and an alarm. The controller includes a processor having circuitry programed to calculate a consciousness score and a memory. The consciousness detection system is configured to periodically conduct at least one response test on the subject to obtain response test results which are used to calculate a consciousness score. The monitor may be configured to display data contained within the memory. The input unit may be configured to allow a user to manually input data to the device. The network module may be configured to allow the device to communicate with a second device for monitoring the relative consciousness of a subject remotely or in conjunction with other patients.

In an exemplary embodiment, a method for monitoring the relative consciousness of a subject is described. The method includes conducting at least one response test on the subject to obtain a plurality of response test results. The response test includes an eye movement test conducted with a camera sensor, and the plurality of response test results are analyzed by comparison to a machine learning module to quantify the eye movement of the subject. The response test is administered by a consciousness detection system. The consciousness detection system includes a controller, the camera sensor, and an alarm. The controller includes a processor having circuitry programmed to calculate a consciousness score and a memory. The method includes recording the response test results in the memory of the processor. The method includes analyzing, with the circuitry of the processor, the response test results to determine a consciousness score. The method also includes triggering an alarm based on the consciousness score, indicating a loss of consciousness. In addition, the method includes analyzing with the machine learning module, the response test results and the consciousness score, to modify the programming of the circuitry such that the accuracy of the method is improved with use. The method further includes repeating the at least one response test at predetermined regularly timed intervals. The repetition is initiated by the processor.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
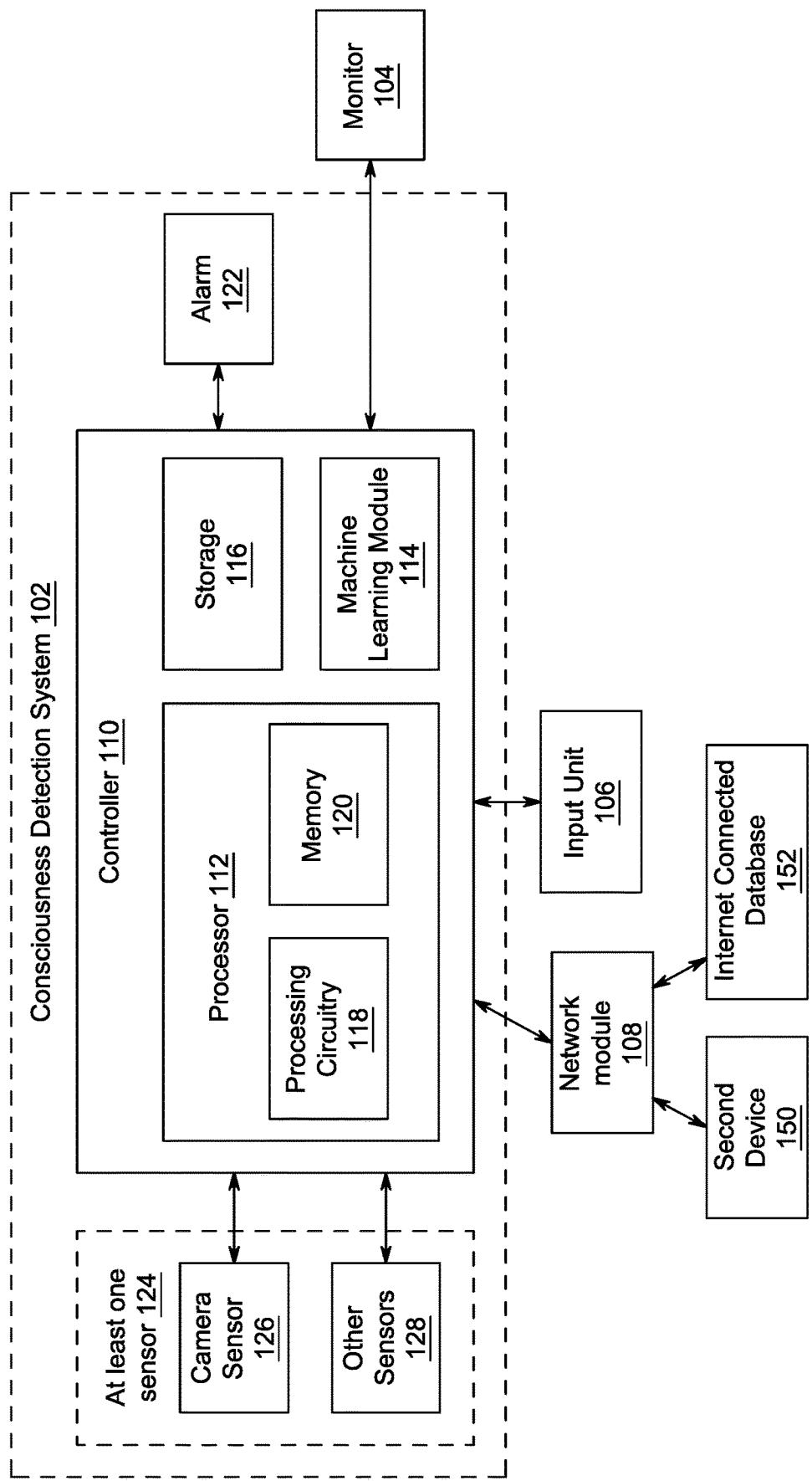
FIG. 1 illustrates a system for monitoring the relative consciousness of a subject, according to certain embodiments of the present disclosure.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms refer to ranges that include the identified value within a margin of 20%, 10%, or preferably 5%, and any values there between.

Aspects of the present disclosure are directed to monitoring the relative consciousness of a subject. The present disclosure uses a machine learning model to significantly improve the monitoring of subjects in an intensive care unit or otherwise being monitored for brain injuries. The present disclosure improves a nurse's work by automatically monitoring the patient's consciousness level and sending alerts to a nurse station for further assessment. Furthermore, the method enables the nurse to get a full history of a subject's (herein also referred to as a "patient") consciousness throughout the patient's stay at the hospital. Since patient monitoring is time-consuming and labor intensive, this disclosure leverages the advanced techniques of computer vision and machine learning for the purpose of enhancing patient care. The system includes a camera sensor for watching the movements of the subject, a pain induction device for stimulating pain, a speaker for sending commands to the subject, and an audio receiver for obtaining verbal responses from the subject. The system can alert nurses to any sudden changes to the patients' consciousness while preserving a full history of the patient's evaluated consciousness.

In various aspects of the disclosure, non-limiting definitions of one or more terms that will be used in the document are provided below.

The term "microcontroller" as used herein refers to a computer component adapted to control a system to achieve certain desired goals and objectives. For example, the microcontroller may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The term "sensor" refers, without limitation, to the component or region of a device which is configured to detect the presence or absence of a measurable parameter. For example, the camera sensor may be a camera configured to capture images or frames. The camera sensor may also be any image sensor or imager that detects and conveys information to form an image by converting variable attenuation of light waves into signals. The camera sensor may also be a device specifically designed to track the motion of a patient's eye and differentiate between various types of eyeball movement, for example the camera sensor may be capable of differentiating between smooth pursuit movements and vestibulo-ocular movements, saccades movements, and vergence movements.

The term 'machine learning' refers to a method of data analysis that automates analytical model building. Machine learning is a branch of computing that uses statistical techniques to give computer systems the ability to learn from data, without being explicitly programmed.

FIG. 1 illustrates a device for monitoring the relative consciousness of a subject, according to certain embodiments of the present disclosure. The device includes, inter alia, a consciousness detection system (CDS) 102, a monitor 104, an input unit 106 and a network module 108.

The CDS 102 is a unit configured to monitor a subject by periodically or continuously conducting at least one response test on the subject to obtain response test results which are used to calculate a consciousness score. The consciousness score may refer to a score obtained by calculating a sum of values associated with three parameters used in measuring the relative consciousness of the subject. The consciousness score may also refer to a score obtained by calculating a sum of values associated with any number of response tests used in measuring the relative consciousness of the subject. The three parameters may include eye-movement, verbal response, and motor response. The three parameters have various values which correspond to levels of consciousness as provided below.

a. Eye movement (Score: 4)
  1. No eye opening
  2. Eye opening to pain
  3. Eye opening to sound
  4. Eyes open spontaneously b. Motor response (Score: 6)
1. No motor response
2. Abnormal extension to pain
3. Abnormal flexion to pain
4. Withdrawal from pain
5. Localizing pain
6. Obeys commands
c. Verbal response (Score: 5)
1. No verbal response
2. Incomprehensible sounds
3. Inappropriate words
4. Confused
5. Orientated Each of the parameters is considered, and values associated with the parameters are identified for the calculation. The conscious score may be in a range of values between three (3) and fifteen (15), with three indicating a deep comatose state and fifteen indicating a fully conscious state.

The at least one response test includes obtaining values associated with the parameters. In an embodiment, the response test includes an eye movement test, a motor response test, and a verbal response test. The CDS 102 includes a controller 110, at least one sensor 124, and an alarm 122. The controller 110 may be configured to conduct the at least one response test, analyze, and record repetitively over a time period x and a frequency y, on the subject, to obtain a plurality of response test results which are used to calculate a consciousness score. The time period x and frequency may be determined by the machine learning module 114.

In an embodiment, the response test may include any interactive test or observational analysis which can be performed on a subject to obtain a value which may be used to calculate a consciousness score. The response test may comprise an auditory function test, a visual function test, an oromotor function test, a communication test, arousal scale tests, a pupillary light response test, a corneal reflex response test, an eye position test, an eye movement test, an oculocephlic reflex test, and a postural response test. The CDS 102 may make a determination as to a patient's relative level of consciousness based on a summation, or weighted summation, of scores associated with the response test.

The controller 110 may refer to any computing device such as a computer, a laptop, a desktop, a cloud server, or the like. The controller 110 may include a processor 112, a machine learning module 114 and a storage 116. The processor 112 may be any logic circuitry such as an integrated circuit (IC) that receives (or fetches) instructions from memory (memory 120) and processes the instructions and generates output. In one or more embodiments, the processor 112 may be a microprocessor unit or a microcontroller unit. Some examples of microprocessor units may include Intel processors (manufactured by Intel Corporation of Mountain View, California), Advanced Micro Devices processors (manufactured by Advanced Micro Devices of Sunnyvale, California), Snapdragon processors (manufactured by Qualcomm, San Diego, California, United States) and similar such processors. In some embodiments, the processor may be a high performance processor configured to handle process intensive instructions associated with machine learning (ML) and artificial intelligence (AI). Examples of high performance processors include AMD Ryzen (manufactured by Advanced Micro Devices of Sunnyvale, California), and Intel Core i9 (manufactured by Intel Corporation of Mountain View, California). The processor 112 may be a single core processor or a multi-core processor that is capable of handling instruction level parallelism and thread level parallelism, and may have different levels of cache. The processor 112 may include processing circuitry 118 that is programmed to calculate the consciousness score.

The memory 120 is a data storage unit having one or more memory chips capable of storing data and allowing any storage location to be directly accessed by the processing circuitry 118. The memory 120 may be a Dynamic Random-Access Memory (DRAM) or any variant thereof. In some embodiments, the memory 120 may be a volatile memory or a non-volatile memory. The processing circuitry 118 may communicate with the memory 120 through IC interconnects (not shown).

The machine learning module 114 may include suitable hardware, set of instructions, or combination of hardware and instructions to support and enable the controller 110 to learn and improve from experience and data without being explicitly programmed. Although the machine learning module 114 is shown as a part of the controller 110, the machine learning module 114 can be implemented external to the controller 110 and communicatively coupled to the controller 110.

The alarm 122 may be a hardware unit configured to generate an alarm in response to a trigger from the processor 112, the alarm being configured to draw the attention of at least one person to the subject. The alarm 122 may be a visual alarm, an auditory alarm, a haptic alarm, or a combination of various alarms.

The at least one sensor 124 may be a sensor for monitoring a subject. The at least one sensor 124 may include a camera sensor 126 and other sensors 128. In some examples, the camera sensor 126 may be a smart camera with a facial recognition based on, for example, efficient-Net deep learning algorithm AI implemented to detect faces and features thereon. In an example, the efficient-Net deep learning algorithm is a convolutional neural network (CNN) pre-trained on images of different faces, taken at different angles and lighting settings, to determine if the eyes are open. The other sensors 128 include a motion sensor, an auditory sensor, a temperature sensor, a pressure sensor, and such sensors to continuously and/or randomly monitor the subject. In implementations, the camera sensor 126 may be positioned to capture the movements of the face and body of the subject.

The monitor 104 may be a hardware device configured to display data contained within the memory 120. The monitor 104 may be an input/output device capable of receiving input as well as providing output, such as, a touch screen. In some examples, the monitor 104 may include a liquid crystal display (LCD), an organic light-emitting diode (OLED) display, an active-matrix organic light-emitting diode (AMOLED) display, or 3D display.

The input unit 106 may be a hardware device configured to allow a user to manually input data to the device 100. Examples of the input unit 106 include, but are not limited to, keyboards, a pointing device, microphones, drawing tablets, a camera, a joystick, a touchscreen, and similar such devices. Output devices may include video displays, graphical displays, speakers, headphones, inkjet printers, laser printers, and 3D printers.

The network module 108 may be an interface to communicatively couple the device 100 to a network through various means including, but not limited to, standard telephone lines, Local Area Networks (LAN), Wide Area Network (WAN) links, broadband connections, wireless connections, or combinations of any or all of the above. The network module 108 may use various communication protocols such as a TCP/IP, Ethernet, IEEE 802.11, WiFi, WiMAX, and similar such protocols. The network module 108 may include a network interface card, a wireless network adapter, a USB network adapter, modem, or any other elements which enable coupling the device 100 with any type of network capable of communication and/or performing the operations described herein. According to the disclosure, the network module 108 provides a communication interface to couple and communicate the device 100 with a second device 150 for monitoring the relative consciousness of the subject.

In operation, the CDS 102 is configured to monitor a subject such as a patient. In one embodiment, the CDS 102 is configured to monitor the subject periodically or on-demand. In some embodiments, the CDS 102 is configured to continuously monitor the subject. When the CDS 102 is monitoring the subject periodically or on-demand, the CDS 102 directs the at least one sensor 124 to continuously capture information associated with the parameters of the subject. Considering the eye movement parameter, in an example, the CDS 102 may use the camera sensor 126 to capture images or frames of the subject. In some examples, the camera sensor 126 may use a facial recognition based efficient-Net deep learning algorithm to detect the patient's face. In cases where the face is not detected, the camera sensor 126 is configured to recapture the frames while ensuring the taken frames have a detectable face using a face detection-based Net deep learning algorithm.

In an implementation, the camera sensor 126 captures continuous frames of the subject's face and body when directed. In periodic or on-demand monitoring, the CDS 102 may conduct at least one response test on the subject to obtain one or more response test results. Considering the eye movement parameter, the CDS 102 conducts the at least one response test by directing the camera sensor 126 to capture frames (video) for an eye movement test. In an aspect, performing the response test includes simply capturing frames of the face. In another aspect, performing the response test includes providing stimulus to the patient. The stimulus includes providing light of varying intensities, providing localized pain, providing verbal instructions to open or close the eyes, etc. The various stimulus is provided when there is no eye movement detected. The camera sensor 126 captures and records the frames of response test results of the subject. The response test results may or may not include the movements of the eyes of the subject. In an example, the camera sensor 126 may preprocess the captured frames to mask out the non-face part of the image. The CDS 102 stores the preprocessed response test results in the memory 120 of the processor 112. The machine learning module 114 analyzes the response test results (obtained from the memory 120 or a direct feed from the camera sensor 126) to determine the movement of the eyes of the subject. In an example, the machine learning module 114 may use deep learning techniques to perform this determination. Based on the determination, the machine learning module 114 analyzes the response test results and quantifies the eye movement of the subject and provides an eye movement consciousness score. In an example, the eye movement consciousness score determines that eye movement has occurred when a patient's eyelids move from a closed position to an open position. In this example the eye movement consciousness score is given as four (4) when there was a spontaneous movement of the patient's eyes, a three (3) if there are movements in the eyes in response to sound stimuli and, two (2) if there was eye movement in response to pain stimuli, and one (1) if there was no eye movement in response to stimuli. The eye movement consciousness score alone may be considered as the consciousness score if other parameters are not considered.

When the eye movement consciousness score is considered as the consciousness score, the processor 112 compares the eye movement consciousness score with a predetermined alert range. In response to determining that the eye movement consciousness score is outside the predetermined alert range, the processor 112 triggers the alarm 122 to generate an alarm indicating a loss of consciousness and drawing the attention of medical personnel.

In an embodiment, the eye movement test may comprise any interactive test or observational analysis which evaluates or attempts to quantify the motion of a subject's eye which can be attributed to a neurological response, both voluntary and involuntary.

In some aspects, the loss of consciousness is determined by comparing the consciousness score against a subject specific alert range. The subject specific alert range may be manually input through the input unit 106 by a user, or be determined by the machine learning module 114 which is further configured to monitor the response test results of a plurality of subject response tests and modify the subject specific alert range to correlate with a confirmed loss of consciousness. In some examples, the CDS 102 triggers the alarm 122 when the consciousness score is outside the subject specific alert range. In some examples, a user (for example, a healthcare professional including doctors, nurses, etc.) may manually correlate and corroborate the response test with a physical examination and input a confirmed loss of consciousness into the controller 110. In an example, the user may input the confirmed loss of consciousness through the input unit 106. In an example, the alarm may include a sound alarm, a visual alarm, a haptic alarm or a combination of alarms. In some examples, the alarm 122 may be a message or an automated call to appropriate personnel (healthcare personnel). The processor 112 repeats the at least one response test at predetermined regularly timed intervals. The predetermined regularly timed intervals refer to an initial default time of delay between the at least one response test and the repeated at least one response test. The predetermined regularly timed intervals may be patient specific and configured to be modified in duration, automatically or manually, during the practice of the method. In embodiments, the machine learning module 114 dynamically modifies the predetermined regularly timed intervals.

Considering the motor response parameter, in an example, the CDS 102 may use the camera sensor 126 and other sensors 128 to monitor the subject. The CDS 102 may conduct the at least one response test on the subject to obtain one or more response test results. The at least one response test includes the CDS 102 instructing the subject to perform some action. For example, the CDS 102 may instruct the subject to lift their index finger, or middle finger, or show a simple gesture. In an example, the CDS 102 may have stored instructions that can be used to instruct the subject. The CDS 102 may communicate through a speaker device (not shown) coupled to the device 100. In an implementation, the camera sensor 126 captures continuous frames of the subject's body. The machine learning module 114 analyzes the response test results (obtained from the memory 120 or using a direct feed from the camera sensor 126) to determine the motor response of the subject. In some examples, the machine learning module 114 uses hand gesture detection and classification based on a deep learning gesture recognition to determine the movements and to classify gestures. Hand gesture detection and classification may be based on Yolo v4 or be accomplished by any deep learning neural network system. The machine learning module 114 uses the captured frames to detect the subject's response using a deep learning model. The deep learning model classifies captured frames into corresponding gesture classes. The machine learning module 114 is trained to detect numbers shown on fingers, and gestures such as thumbs up and down, captured using the camera sensor. If the machine learning module 114 detects that the response of the gesture shown by the subject is correct based on the given prompt, then the machine learning module 114 provides a motor response consciousness score of six (6). Otherwise, the CDS 102 may provide another instruction to the subject such as to have them flex their arm. The camera sensor 126 captures continuous frames of the subject's body as a part of the response test. If the machine learning module 114 detects the subject's muscles flexing, when the subject is asked to bend his/her arms, Bluetooth connected sensors attached to each of the two arms may detect the arm bending response and transmit the signal to the CDS 102. If an arm flex is detected, the CDS 102 provides the subject with the motor response consciousness score of four (4). If an abnormal or weak flex is detected by the Bluetooth connected sensors, then the CDS 102 assigns the subject with the motor response consciousness score of three (3). If no response from the patient is detected then the CDS 102 initiates a pain stimulation through a Thermal Pain Stimulator (TRS), and directs the camera sensor 126 to capture continuous frames of the subject's body. The machine learning module 114 analyzes the response test results to determine any movements in the subject's body. If there are movements, the machine learning module 114 provides the motor response consciousness score of two (2). Otherwise, the machine learning module 114 provides the motor response consciousness score of one (1).

In another implementation of the motor response test, if the machine learning module 114 detects that the response of the gesture shown by the subject is correct in the response test results, then the machine learning module 114 provides a motor response consciousness score of six (6). If no response from the patient is detected then the CDS 102 initiates pain stimulation through TRS to a portion of the patient's body such that the natural response to this pain would be for the patient move their arm towards the stimulated site. The camera sensor 126 captures continuous frames of the subject's body as a part of the response test. If the machine learning module 114 detects the subject's muscles flexing fully such that an arm moves towards the localized site of pain, the CDS 102 provides the subject the motor response consciousness score of five (5). If the machine learning module 114 detects the subject's muscles flexing correctly, but insufficiently to fully reach the site of stimulation, or if the patient reacts by normally withdrawing from the pain, then the CDS 102 assigns the subject with the motor response consciousness score of four (4). If the machine learning module 114 detects the subject's muscles flexing in a fashion inconsistent with an appropriate withdraw response then the CDS 102 assigns the subject with the consciousness score of three (3). If the machine learning module 114 detects the subject's muscles extending instead of withdrawing, the CDS 102 assigns the subject with the consciousness score of two (2). If no response from the patient is detected then the CDS 102 assigns the subject with the consciousness score of (1).

Considering the verbal response parameter, in an example, the CDS 102 may use the camera sensor 126 and other sensors 128 to monitor the subject. The CDS 102 may conduct the at least one response test on the subject to obtain one or more response test results. The at least one response test may include the CDS 102 asking the subject some basic questions. For example, the CDS 102 may ask the subject to tell it the current year or the subject's name. In an example, the CDS 102 may have stored questions that can be used to ask the subject. The CDS 102 may communicate through a speaker device (not shown) coupled to the device 100. In an implementation, the CDS 102 uses the camera sensor 126 to capture continuous frames of the subject's face in addition to a microphone device (not shown) to capture a verbal response. The processor 112 may process the verbal response using the speech recognition application Whisper, or any similar speech recognition system, to obtain a transcribed text from the patient speech, and compare the response with actual answers using key words. When the response result is close to the correct answer, the CDS 102 provides a verbal response consciousness score of five (5). If the response test result received is not close to the correct answer, the CDS 102 provides the verbal response consciousness score of four (4). If the response test result includes an unrelated conversation, the CDS 102 provides the verbal response consciousness score of three (3). If the response test result received includes a non-understandable answer, the CDS 102 provides the verbal response consciousness score of two (2). If the response test does not elicit any response, the CDS 102 provides the verbal response consciousness score of one (1).

In some embodiments, the CDS 102 may utilize the machine learning module 114 to evaluate the coherency of the verbal response test results. If the machine learning module 114 determines that the response given by the patient is a coherent statement which does not answer the prompt, then the CDS 102 provides the verbal response consciousness score of (4). If the machine learning module 114 determines that the response given by the patient is a coherent statement which demonstrates that the patient is not confused, then the CDS 102 provides the verbal response consciousness score of five (5).

In a preferable embodiment, the system issues an audible command, message or signal. Preferably, an audible command is initiated instructing the patient to repeat a simple sentence. The patient's response is recorded and compared, with a processor of the system, with the original instruction. A coherence factor is derived by comparing the patient's repeated message with a saved message. A coherence score can be derived based on clarity of speech, number of words correctly repeated, sound intensity of the patient's response, total response time beginning after completion of the audible command to receipt of the patient's response, and/or syllabic correspondence (the number of syllables detected/recorded in comparison to the actual number of syllables in the message).

The eye movement consciousness score, the motor response consciousness score, and the verbal response consciousness score are summated to determine a final consciousness score. For example, if a subject is opening their eyes spontaneously (eye movement consciousness score=5), responding to localized pain (the motor response consciousness score=5) and is providing confused answers (the verbal response consciousness score=4), the final conscious score is determined to be 5+5+4=14, which indicates a high level of consciousness. In some embodiments, one or more of the eye movement consciousness score, the motor response consciousness score, and the verbal response consciousness score may be considered to determine the final consciousness score. For example, the eye movement consciousness score alone may be considered or the eye movement consciousness score may be considered along with the verbal response consciousness to determine the final consciousness score.

In another embodiment of the present invention, the responsiveness measurement of a subject includes at least two concurrent response inputs. For example, an eye-opening response and a verbal response. A concurrent response such that an eye-opening response having a high Glasgow Coma Scale score (e.g., spontaneous eye-opening) together with a verbal response having a high Glasgow coma score, (e.g., concurrent reply) may be weighted more heavily towards a determination of responsiveness. Key to the usefulness of concurrent measurement is any time delay or time differential between the first and second responses. For example, administration of a tactile stimulus to an appendage and/or the torso of a subject and/or a verbal command/stimulus may elicit both an eye-opening movement and a verbal response. The timing of first and second responses is measured. Any differential between eye-movement and verbal response may be used as a basis for weighting the consciousness scale. Typically, lesser delay, and preferably no delay, provides a weighting factor of 1.0 whereas differentials between a first recordation of an eye-movement response and a first recordation of a verbal response provides a fractional weighting which reduces the consciousness score. The verbal response may be measured and/or recorded with conventional recording devices (not pictured).

In some embodiments, when the CDS 102 is continuously monitoring the subject, the aforementioned process is continuously performed, that is without breaks over a period of time. The final consciousness score is determined as described above.

In some implementations, each of the eye movement consciousness score, the motor response consciousness score, the verbal response consciousness score and the final consciousness score may be displayed on the monitor 104.

In some aspects, the machine learning module 114 may automatically modify the predetermined alert range, the machine learning module 114 being configured to improve the accuracy of the response test by analyzing the one or more response test results and associated predetermined alert ranges of the one or more response tests stored in the memory 120. In some aspects, the machine learning module 114 is configured to improve the accuracy of the response test by comparing the response test results and associated predetermined alert ranges of a plurality of response tests stored in the memory 120. In some aspects, the machine learning module 114 is configured to analyze the response test results and the consciousness score, to modify the programming of the processing circuitry such that the accuracy of the monitoring of subject consciousness is improved with continued use.

In some aspects, the processor 112 is configured to upload the plurality of response test results and the associated predetermined alert ranges of a plurality of response test results to an internet connected database 152. The internet connected database 152 is configured to receive and store the plurality of response test results and the associated predetermined alert ranges of the plurality of response test results. Also, the processor 112 is further configured to download response test results and associated predetermined alert ranges from the internet connected database 152 and store them in the memory 120.

In some aspects, the CDS 102 allows monitoring of the subject from the second device 150 through the network module 108.

Figure 2A:
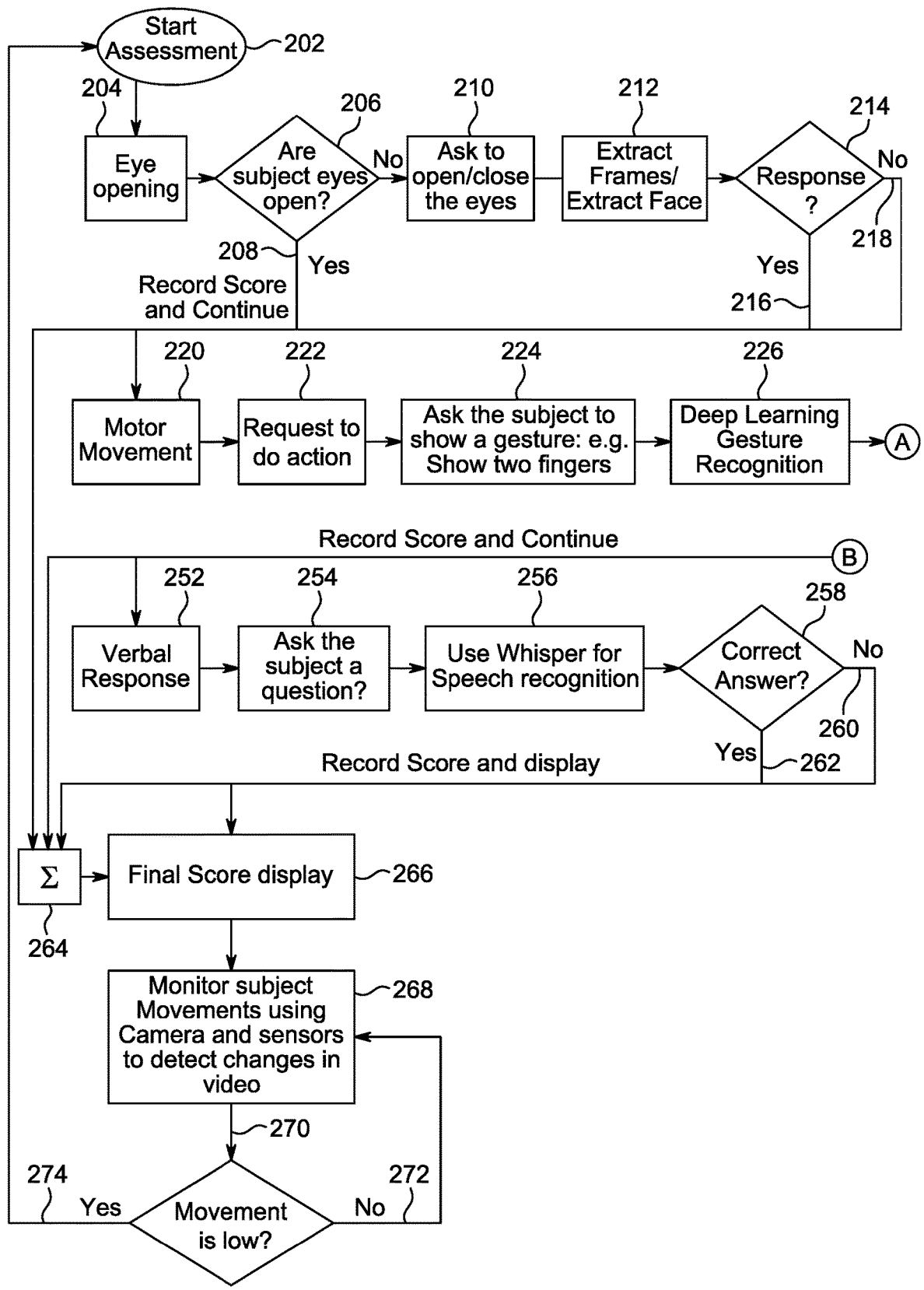
FIG. 2A is a flow diagram for monitoring the relative consciousness of a subject according to certain embodiments of the present disclosure.
Figure 2B:
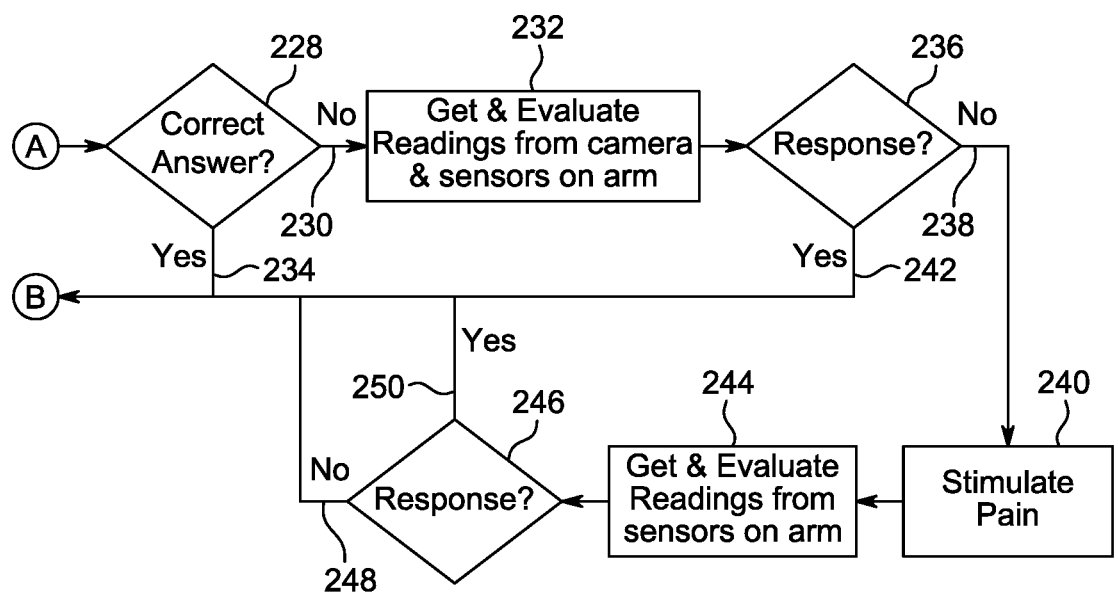
FIG. 2B is a flow diagram for the evaluating a nonverbal test response according to certain embodiments of the present disclosure.

FIG. 2 is a flow diagram for monitoring the relative consciousness of a subject. In step 202, an assessment for monitoring the relative consciousness of a subject is initiated. In step 204, the CDS 102 directs the camera sensor 126 to monitor the eye movement parameter including eye opening and eye closing. In step 206, the machine learning module 114 determines if the subject's eyes are moving or not. If the machine learning module 114 determines that the subject's eyes are moving, the machine learning module 114 provides a score and records the eye movement consciousness score and the flow moves to step 220 or step 264. If the subject eyes are not moving, in step 210, the CDS 102 provides a stimuli, for example, by asking the subject to open/close their eyes. In step 212, the camera sensor 126 extracts frames of the subject's face. In step 214, the machine learning module 114 may determine if there was any response from the subject. If the machine learning module 114 determines that the eyes moved, the eye movement consciousness score is generated and recorded, and the flow moves to step 220 or step 264. If the machine learning module 114 determines that the eyes were not moving, the flow moves to step 264 through step 218.

In step 220, the CDS 102 directs the camera sensor 126 to monitor motor movements of the subject. In step 222, a stimuli is provided, for example, by asking the subject to perform an action. For example, in step 224, the subject is asked to show a gesture, for example to show two fingers. In step 226, the machine learning module 114 uses deep learning gesture recognition to determine the gesture. In step 228, the machine learning module 114 determines whether the gesture is correct or not. If the gesture is not correct, in step 232 the CDS 102 may provide another instruction to the subject such as to perform arm flexing, and obtain and evaluate the readings from the camera sensor 126 and from the other sensors 128 such as Bluetooth sensors under the subject's arms. If there was a motor response, the machine learning module 114 determines and records a motor response score, and the flow moves to step 252 or step 264. If there was no motor response, the flow moves to step 240. In step 240, a pain stimulus is provided. In step 244, the machine learning module 114 obtains and evaluates the readings from the camera sensor 126 and from the other sensors 128. In step 246, the machine learning module 114 may determine if there was any motor response. If there was a motor response, the machine learning module 114 generates and records the motor response consciousness score, and the flow moves to step 252 or step 264. If there was no motor response, the flow moves to step 252 or steps 264.

In step 252, the CDS 102 directs the other sensors 128 to monitor the verbal responses of the subject. In step 254, a stimuli is provided, for example, by asking the subject a question, prompting the subject to respond to the question. In step 256, the other sensors 128 such as a microphone, monitor the subject for a response and perform speech recognition on the recorded response. In step 258, the controller 110 may determine if there was a correct answer to the question. If there was no response, in step 260, the flow moves to step 264. If there was a response, the controller 110 provides and records the verbal response consciousness score, and the flow moves to step 264. In an example, the CDS 102 provides a verbal response consciousness score of five (5). If the response test result received is not close to the correct answer, the CDS 102 provides the verbal response consciousness score of four (4).

If the response test result includes an unrelated conversation, the CDS 102 provides the verbal response consciousness score of three (3). If the response test result received includes a non-understandable answer, the CDS 102 provides the verbal response consciousness score of two (2). If the response test result received does not have any response, the CDS 102 provides the verbal response consciousness score of one (1).

In step 264, the CDS 102 determines a final consciousness score by adding the individual scores of each of the parameters. In step 266, the final consciousness score is displayed on the monitor 104. In step 268, the CDS 102 continues to monitor the subject movements using the camera sensor 126 to detect any changes. In step 270, the CDS 102 may determine if the movement is low. If the movement is low, the flow moves back to step 268 to continue monitoring. If the movement is not low, the flow moves to step 202 to restart the assessment.

Figure 3:
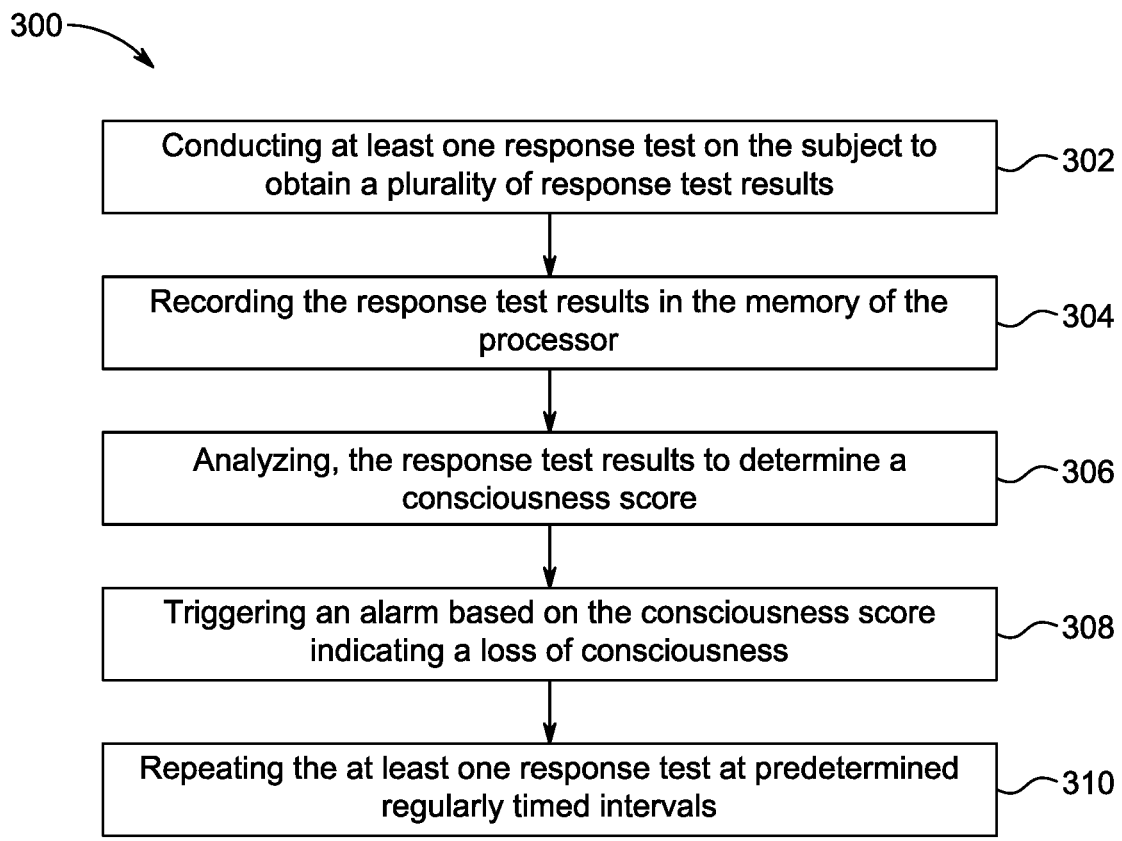
FIG. 3 is a process flow for monitoring the relative consciousness of a subject, according to certain embodiments of the present disclosure.

FIG. 3 is a process flow for monitoring the relative consciousness of a subject, according to some embodiments.

Step 302 includes conducting at least one response test on the subject to obtain a plurality of response test results. The at least one response test may include an eye movement test, a motor response test and a verbal response test. The eye movement test may be conducted with the camera sensor 126, and the plurality of response test results may be analyzed by comparison to a machine learning module 114 to quantify the eye movement of the subject. The response test may be administered by the CDS 102. The CDS 102 includes a controller 110, a camera sensor 126 and an alarm 122. The controller 110 includes a processor 112 having processing circuitry 118 programed to calculate a consciousness score and a memory 120.

Step 304 includes recording the response test results in the memory 120 of the processor 112. Step 306 includes analyzing, with the processing circuitry 118 of the processor 112, the response test results to determine a consciousness score.

Step 308 includes triggering an alarm when the consciousness score indicates a loss of consciousness.

Step 310 includes repeating the at least one response test at predetermined regularly timed intervals. The repetition is initiated by the processor 112. The predetermined regularly timed intervals are dynamically modified by the machine learning module 114. In some embodiments, the processor 112 is instructed to carry out the repeating of the at least one response test, analyzing the response test results, and recording the results, repeatedly over a time period x and a frequency y.

In some embodiments, the loss of consciousness is determined by comparing the consciousness score against a predetermined alert range, and the alarm 122 is triggered by a consciousness score outside the predetermined alert range. The predetermined alert range is automatically modified by the machine learning module 114 which is further configured to improve the accuracy of the response test by analyzing the plurality of response test results and associated predetermined alert ranges of a plurality of response tests stored in the memory 120. In some embodiments, the loss of consciousness is determined by comparing the consciousness score against a subject specific alert range. The subject specific alert range is determined by the machine learning module 114 which is further configured to monitor the response test results of a plurality of subject response tests and modify the subject specific alert range to correlate with a confirmed loss of consciousness. The alarm 122 is triggered by a consciousness score outside the subject specific alert range. In some embodiments, the confirmed loss of consciousness is manually input to the controller 110 and correlated with an individual response test by a user.

The processor 112 is configured to upload the plurality of response test results and the associated predetermined alert ranges of a plurality of response test results to an internet connected database 152. The internet connected database 152 is configured to receive and store the plurality of response test results and the associated predetermined alert ranges of the plurality of response test results. The processor 112 is further configured to download response test results and associated predetermined alert ranges from the internet connected database 152 and store them in the memory 120.

The machine learning module 114 is further configured to improve the accuracy of the response test by comparing the response test results and associated predetermined alert ranges of a plurality of response tests stored in the memory 120.

Figure 4:
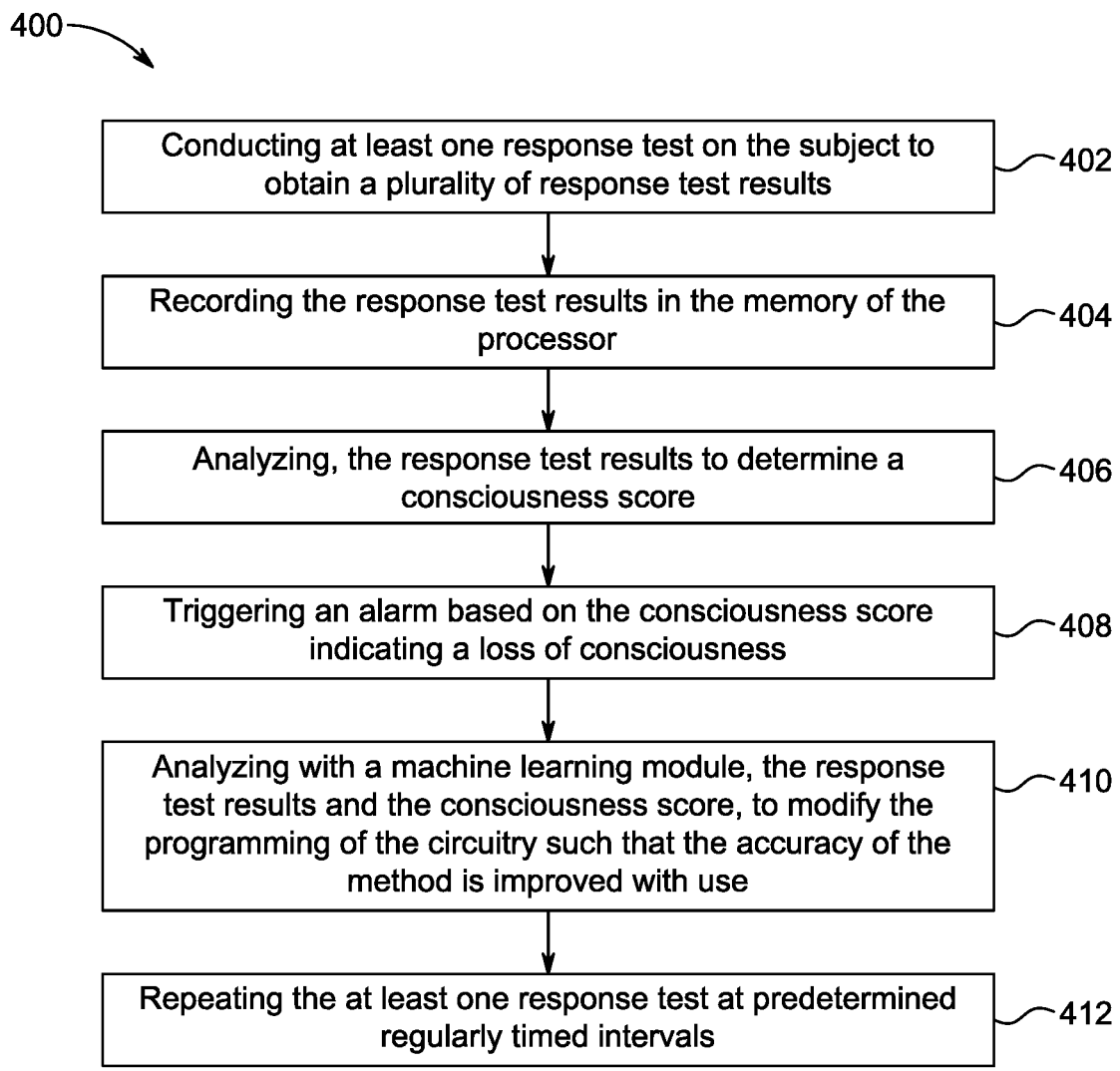
FIG. 4 is a process flow for monitoring the relative consciousness of a subject, according to certain embodiments of the present disclosure.

FIG. 4 is a process flow for monitoring the relative consciousness of a subject, according to some embodiments.

Step 402 includes conducting at least one response test on the subject to obtain a plurality of response test results. The response test includes an eye movement test conducted with a camera sensor, and the plurality of response test results are analyzed by comparison to a machine learning module 114 to quantify the eye movement of the subject. The response test is administered by the CDS 102. The CDS 102 includes a controller, the camera sensor 126 and an alarm 122. The controller 110 includes a processor 112 having processing circuitry 118 programed to calculate a consciousness score and a memory 120.

Step 404 includes recording the response test results in the memory 120 of the processor 112.

Step 406 includes analyzing, with the processing circuitry 118 of the processor 112, the response test results to determine a consciousness score.

Step 408 includes triggering an alarm based on the consciousness score indicating a loss of consciousness.

Step 410 includes analyzing with the machine learning module 114, the response test results and the consciousness score, to modify the programming of the circuitry such that the accuracy of the method is improved with use.

Step 412 includes repeating the at least one response test at predetermined regularly timed intervals. The repetition is initiated by the processor 112. The predetermined regularly timed intervals are dynamically modified by the machine learning module 114. The predetermined alert range is automatically modified by the machine learning module 114 which is further configured to improve the accuracy of the response test by analyzing the plurality of response test results and associated predetermined alert ranges of a plurality of response tests stored in the memory 120.

Figure 5:
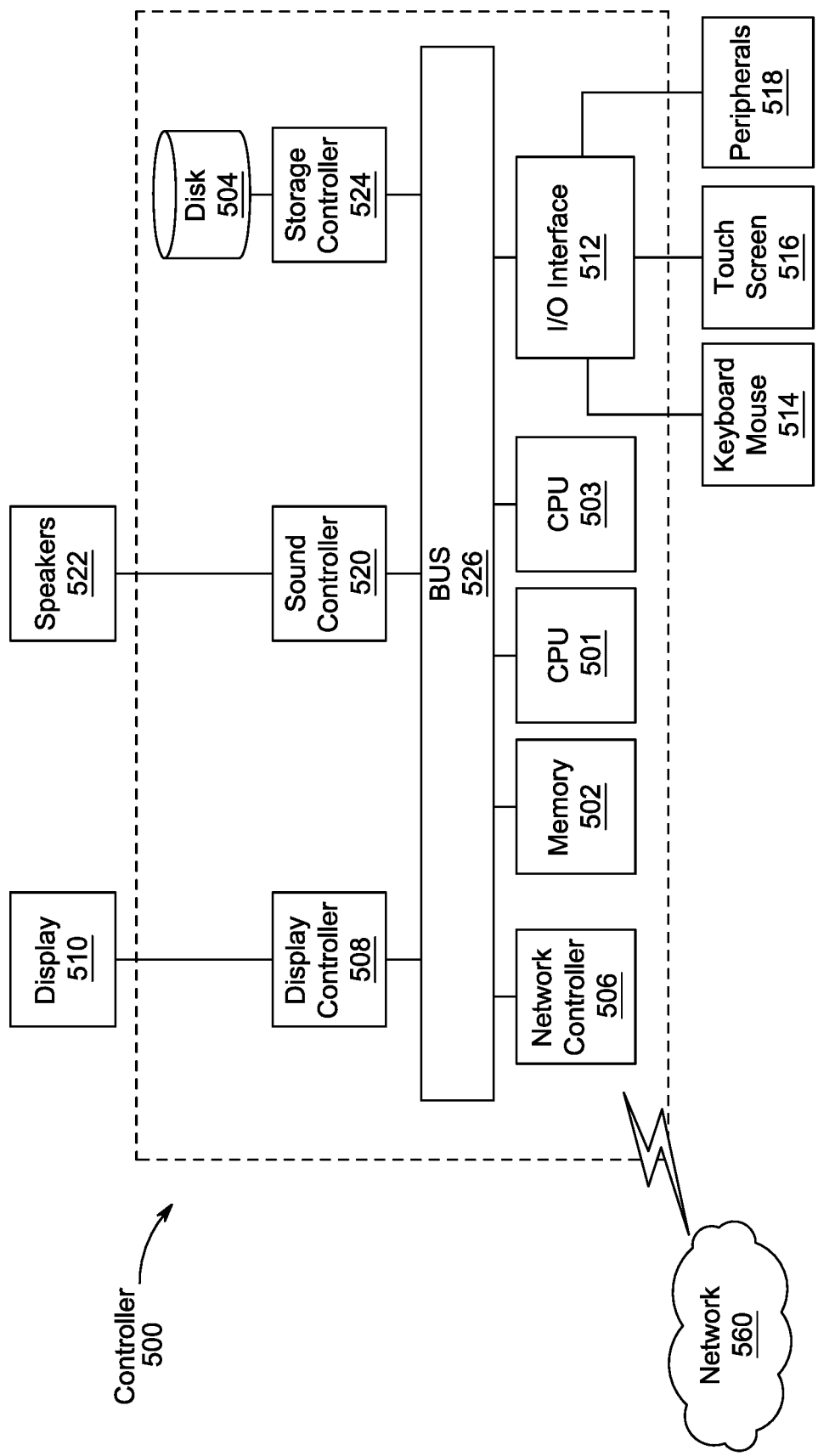
FIG. 5 is an illustration of a non-limiting example of details of computing hardware used in the computing system, according to certain embodiments of the present disclosure.

In FIG. 5, a controller 500 is described as representative of the controller 110 of FIG. 1 in which the CDS 102 is a computing device which includes a CPU 501 which performs the processes described above/below. FIG. 5 is an illustration of a non-limiting example of details of computing hardware used in the computing system, according to exemplary aspects of the present disclosure. In FIG. 5, a controller 500 is described which is a computing device (that device 100 and/or the CDS 102) and includes a CPU 501 which performs the processes described above/below. The process data and instructions may be stored in memory 502. These processes and instructions may also be stored on a storage medium disk 504 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 501, 503 and an operating system such as Microsoft Windows, UNIX, Solaris, LINUX, Apple MAC-OS and other systems known to those skilled in the art.

The hardware elements utilized in order to achieve the computing device may be realized by various circuitry elements, known to those skilled in the art. For example, CPU 501 or CPU 503 may be a Xenon or Core processor from Intel of America or an Opteron processor from AMD of America, or may be other processor types that would be recognized by one of ordinary skill in the art. Alternatively, the CPU 501, 503 may be implemented on an FPGA, ASIC, PLD or implemented using discrete logic circuits, as one of the ordinary skill in the art would recognize. Further, CPU 501, 503 may be implemented as multiple processors cooperatively working in parallel to perform the instructions of the inventive processes described above.

The computing device in FIG. 5 also includes a network controller 506, such as an Intel Ethernet PRO network interface card from Intel Corporation of America, for interfacing with network 560. As can be appreciated, the network 560 can be a public network, such as the Internet, or a private network such as an LAN or WAN network, or any combination thereof and can also include PSTN or ISDN sub-networks. The network 560 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 508, such as a NVIDIA GeForce GTX or Quadro graphics adaptor from NVIDIA Corporation of America, for interfacing with display 510, such as a Hewlett Packard HPL2445w LCD monitor. A general purpose I/O interface 512 may interface with a keyboard and/or mouse 514 as well as a touch screen panel 516, on or separate from display 510. The General purpose I/O interface may also connect to a variety of peripherals 518 including printers and scanners, such as an OfficeJet or DeskJet from Hewlett Packard.

A sound controller 520 may also be provided in the computing device, such as a Sound Blaster X-Fi Titanium from Creative, to interface with speakers/microphone 522 thereby providing sounds, instructions, and/or music.

The general-purpose storage controller 524 connects the storage medium disk 504 with communication bus 526, which may be an ISA, EISA, VESA, PCI, or similar, for interconnecting all of the components of the computing device. A description of the general features and functionality of the display 510, keyboard and/or mouse 514, as well as the display controller 508, storage controller 524, network controller 506, sound controller 520, and general purpose I/O interface 512 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 6.

Figure 6:
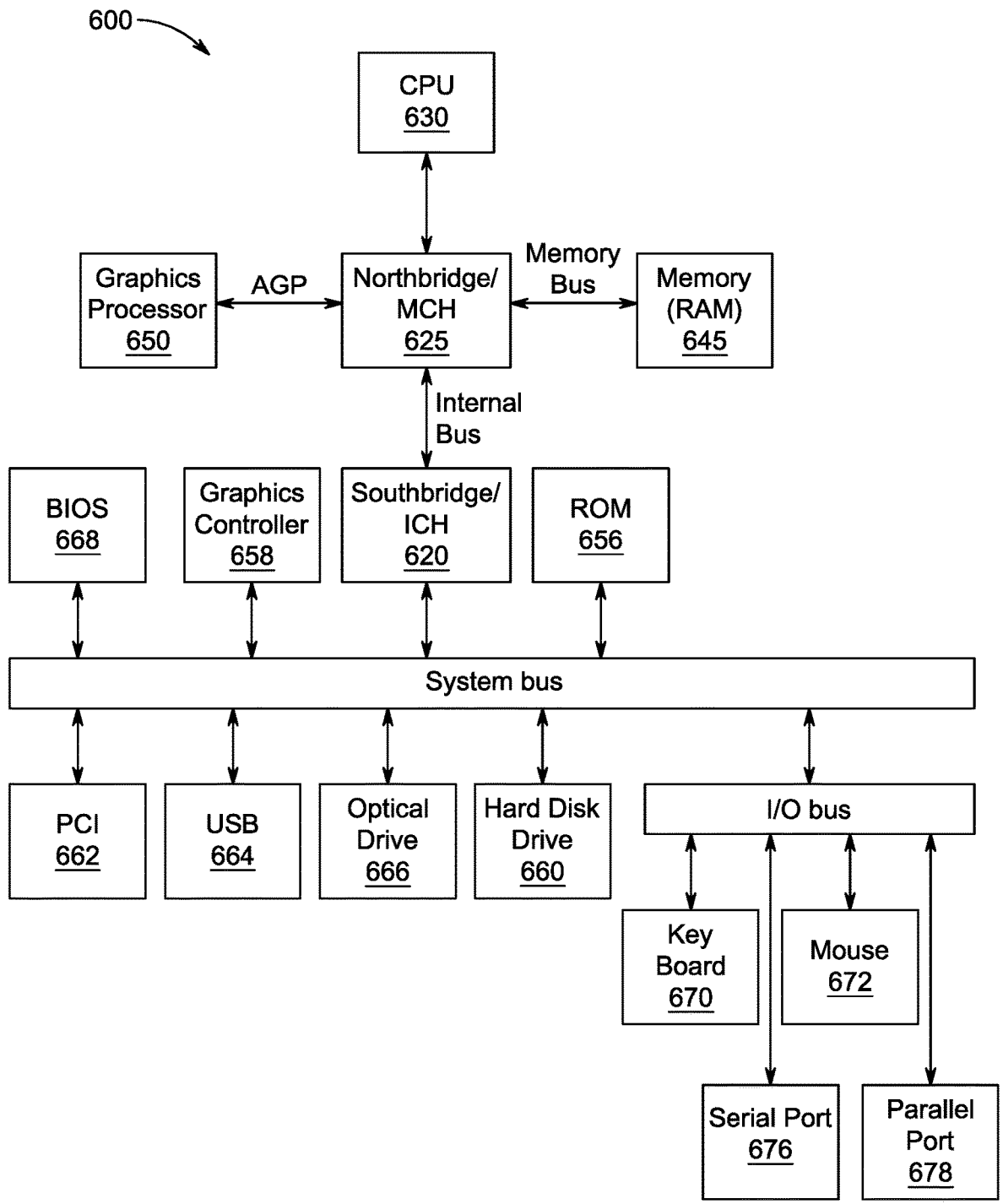
FIG. 6 is an exemplary schematic diagram of a data processing system used within the computing system, according to certain embodiments of the present disclosure.

FIG. 6 shows a schematic diagram of a data processing system 600 used within the computing system, according to exemplary aspects of the present disclosure. The data processing system 600 is an example of a computer in which code or instructions implementing the processes of the illustrative aspects of the present disclosure may be located.

In FIG. 6, data processing system 600 employs a hub architecture including a north bridge and memory controller hub (NB/MCH) 625 and a south bridge and input/output (I/O) controller hub (SB/ICH) 620. The central processing unit (CPU) 630 is connected to NB/MCH 625. The NB/MCH 625 also connects to the memory 645 via a memory bus, and connects to the graphics processor 650 via an accelerated graphics port (AGP). The NB/MCH 625 also connects to the SB/ICH 620 via an internal bus (e.g., a unified media interface or a direct media interface). The CPU Processing unit 630 may contain one or more processors and even may be implemented using one or more heterogeneous processor systems.

Figure 7:
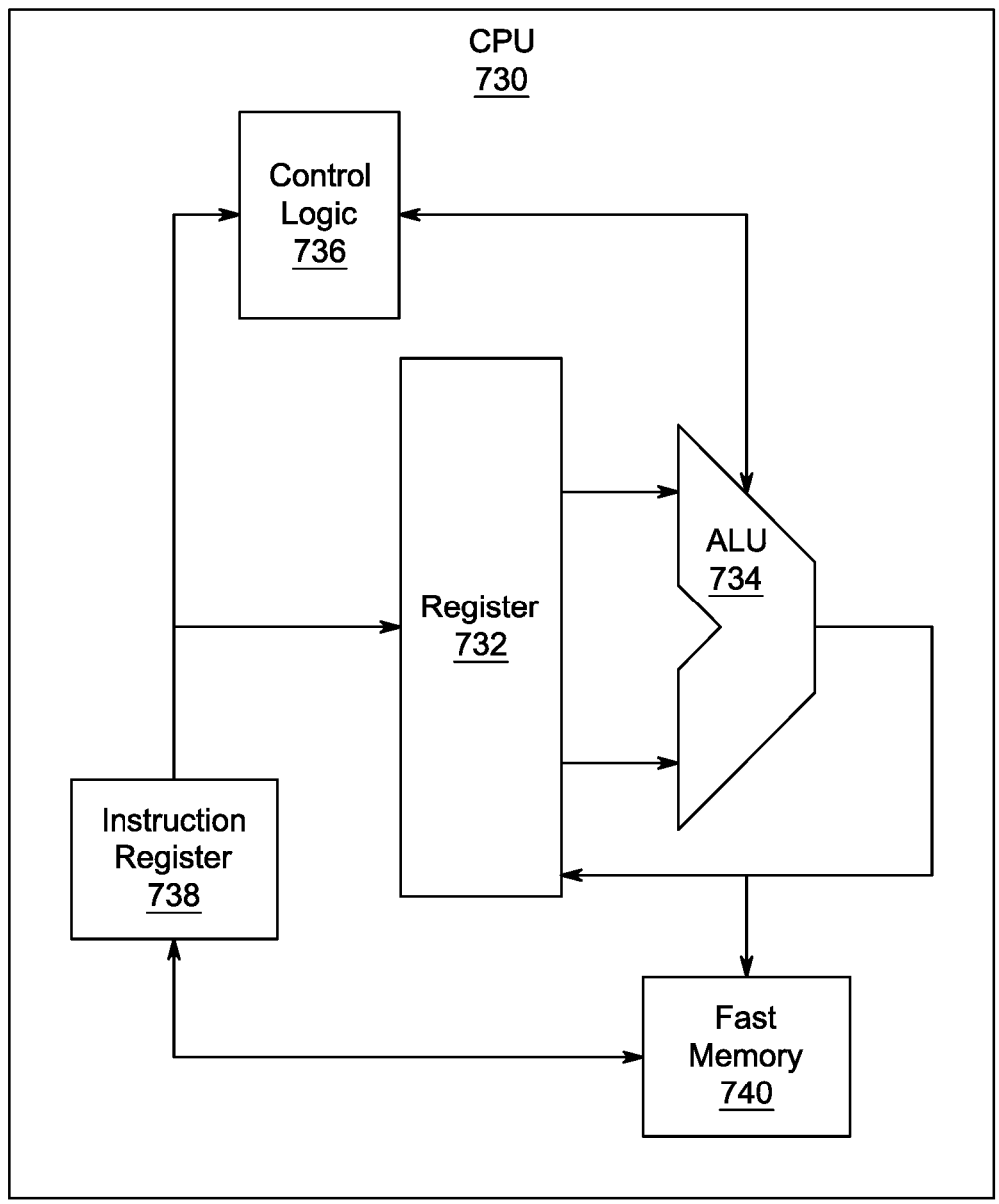
FIG. 7 is an exemplary schematic diagram of a processor used with the computing system, according to certain embodiments of the present disclosure.

For example, FIG. 7 shows one aspect of the present disclosure of CPU 630. In that aspect the instruction register 738 retrieves instructions from the fast memory 740. At least part of these instructions are fetched from the instruction register 738 by the control logic 736 and interpreted according to the instruction set architecture of the CPU 730. Part of the instructions can also be directed to the register 732. In one aspect of the present disclosure the instructions are decoded according to a hardwired method, and in another aspect of the present disclosure the instructions are decoded according to a microprogram that translates instructions into sets of CPU configuration signals that are applied sequentially over multiple clock pulses. After fetching and decoding the instructions, the instructions are executed using the arithmetic logic unit (ALU) 734 that loads values from the register 732 and performs logical and mathematical operations on the loaded values according to the instructions. The results from these operations can be fed back into the register and/or stored in the fast memory 740. According to certain aspects of the present disclosure, the instruction set architecture of the CPU 730 can use a reduced instruction set architecture, a complex instruction set architecture, a vector processor architecture, or a very large instruction word architecture. Furthermore, the CPU 730 can be based on the Von Neuman model or the Harvard model. The CPU 730 can be a digital signal processor, an FPGA, an ASIC, a PLA, a PLD, or a CPLD. Further, the CPU 730 can be an x86 or x64 processor by Intel or by AMD; an ARM processor, a Power architecture processor by, e.g., IBM; a SPARC architecture processor by Sun Microsystems or by Oracle; or other known CPU architecture.

Referring back to FIG. 6, the data processing system 600 can include that the SB/ICH 620 is coupled through a system bus to an I/O Bus, a read only memory (ROM) 656, universal serial bus (USB) port 664, a flash binary input/output system (BIOS) 668, and a graphics controller 658. PCI/PCIe devices can also be coupled to SB/ICH 620 through a PCI bus 662.

The PCI devices may include, for example, Ethernet adapters, add-in cards, and PC cards for notebook computers. The Hard disk drive and CD-ROM can use, for example, an integrated drive electronics (IDE) or serial advanced technology attachment (SATA) interface. In one aspect of the present disclosure the I/O bus can include a super I/O (SIO) device.

Further, the hard disk drive (HDD) 660 and optical drive 666 can also be coupled to the SB/ICH 620 through a system bus. In one aspect of the present disclosure, a keyboard 670, a mouse 672, a parallel port 678, and a serial port 676 can be connected to the system bus through the I/O bus. Other peripherals and devices that can be connected to the SB/ICH 620 using a mass storage controller such as SATA or PATA are an Ethernet port, an ISA bus, an LPC bridge, SMBus, a DMA controller, and an Audio Codec.

Moreover, the present disclosure is not limited to the specific circuit elements described herein, nor is the present disclosure limited to the specific sizing and classification of these elements. For example, those skilled in the art will appreciate that the circuitry described herein may be adapted based on changes to battery sizing and chemistry or based on the requirements of the intended back-up load to be powered.

Figure 8:
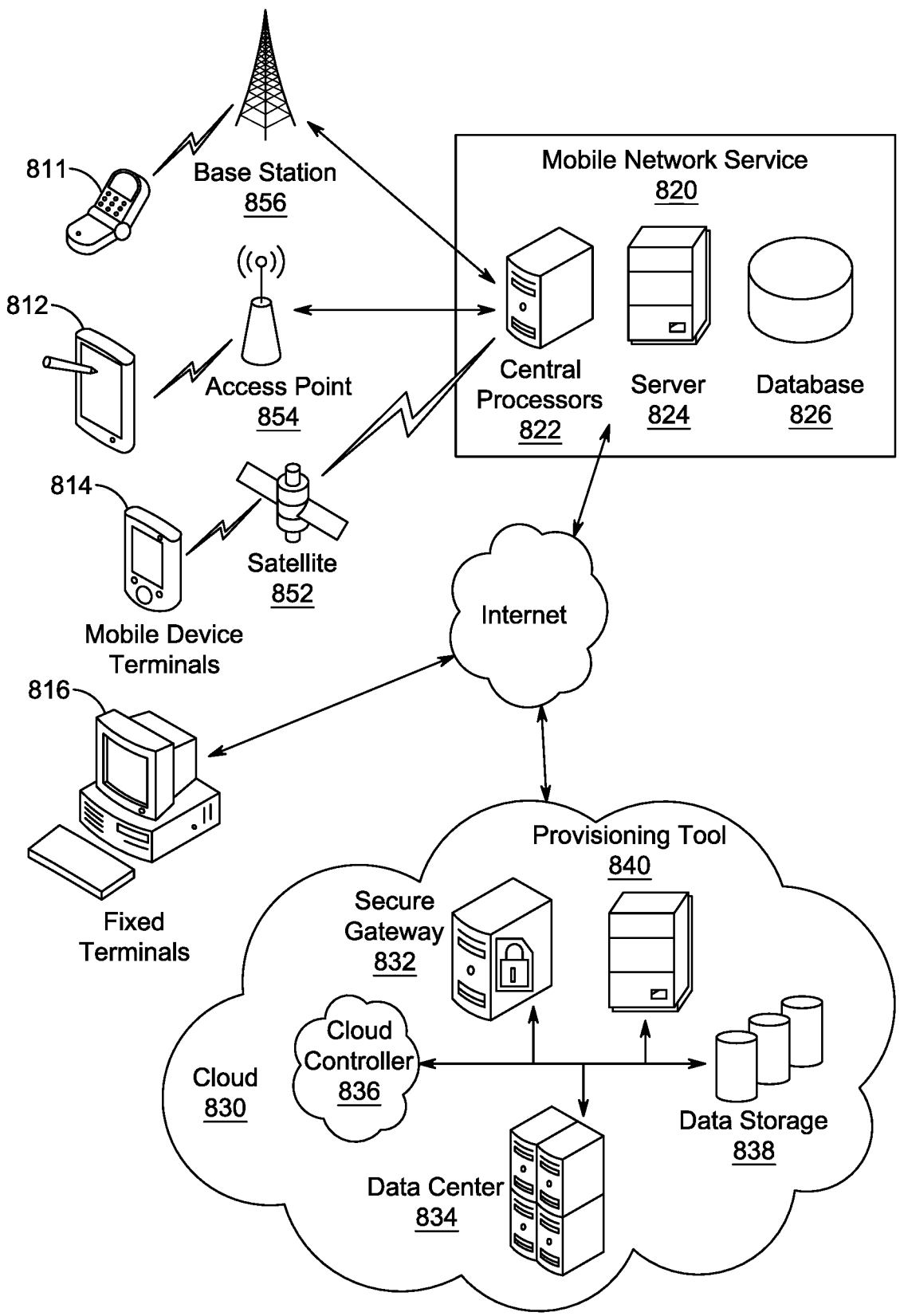
FIG. 8 is an illustration of a non-limiting example of distributed components which may share processing with the controller, according to certain embodiments of the present disclosure.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 8, in addition to various human interface and communication devices (e.g., display monitors, smart phones, tablets, personal digital assistants (PDAs)). More specifically, FIG. 8 illustrates client devices including smart phones 811, tablets 812, mobile device terminals 814 and fixed terminals 816. These client devices may be commutatively coupled with a mobile network service 820 via base station 856, access point 854, satellite 852 or via an internet connection. Mobile network service 820 may comprise central processors 822, servers 824, and databases 826. Fixed terminals 816 and mobile network service 820 may be commutatively coupled via an internet connection to functions in cloud 830 that may comprise security gateway 832, data center 834, cloud controller 836, data storage 838 and provisioning tool 840. The network may be a private network, such as a LAN or WAN, or may be a public network, such as the Internet. Input to the system may be received via direct user input and received remotely either in real-time or as a batch process. Additionally, some aspects of the present disclosure may be performed on modules or hardware not identical to those described. Accordingly, other aspects of the present disclosure are within the scope that may be claimed.

The above-described hardware description is a non-limiting example of corresponding structure for performing the functionality described herein. Obviously, numerous modifications and variations of the present disclosure are possible in light of the above teachings. It is therefore to be understood that within the scope of the appended claims, the invention may be practiced otherwise than as specifically described herein.

The invention claimed is:

1. A method for monitoring the relative consciousness of a subject, the method comprising:
conducting at least one response test on the subject to obtain a plurality of response test results, wherein the response test comprises an eye movement test conducted with a camera sensor, and the plurality of response test results are analyzed by comparison to a machine learning module to quantify the eye movement of the subject, wherein the response test is administered by a consciousness detection system, wherein the consciousness detection system comprises a controller, the camera sensor and an alarm, wherein the controller comprises a processor having circuitry programed to calculate a consciousness score and a memory;
recording the response test results in the memory of the processor;
analyzing, with the circuitry of the processor, the response test results to determine a consciousness score;
triggering an alarm based on the consciousness score indicating a loss of consciousness; and
repeating the at least one response test at predetermined regularly timed intervals, wherein the repetition is initiated by the processor,
wherein a loss of consciousness is determined by:
comparing the consciousness score against a predetermined alert range, the predetermined alert range being automatically modified by the machine learning module which is further configured to improve the accuracy of the response test by analyzing the plurality of response test results and associated predetermined alert ranges of a plurality of response tests stored in the memory; and
the alarm is triggered by a consciousness score outside the predetermined alert range.

2. The method of claim 1, wherein the processor has further instructions to carry out the repeating of the at least one response test, analyzing, and recording repeatedly over a time period x and a frequency y.

3. The method of claim 2, wherein the response test comprises:
an eye movement test;
a motor response test; and
a verbal response test.

4. The method of claim 1, wherein the predetermined regularly timed intervals are dynamically modified by the machine learning module.

5. The method of claim 1, wherein the processor is configured to upload the plurality of response test results and the associated predetermined alert ranges of a plurality of response test results to an internet connected database, wherein the internet connected databased is configured to receive and store the plurality of response test results and the associated predetermined alert ranges of the plurality of response test results; and
the processor is further configured to download response test results and associated predetermined alert ranges from the internet connected database and store them in the memory.

6. The method of claim 5, wherein the machine learning module is further configured to improve the accuracy of the response test by comparing the response test results and associated predetermined alert ranges of a plurality of response tests stored in the memory.

7. The method of claim 4, wherein a loss of consciousness is determined by:
comparing the consciousness score against a subject specific alert range, wherein the subject specific alert range is determined by the machine learning module which is further configured to monitor the response test results of a plurality of subject response tests and modify the subject specific alert range to correlate with a confirmed loss of consciousness; and
the alarm is triggered by a consciousness score outside the subject specific alert range.

8. The method of claim 7, wherein a confirmed loss of consciousness is manually input to the controller and correlated with an individual response test by a user.

9. A device for monitoring the relative consciousness of a subject, the device comprising:

at least one sensor of a consciousness detection system, wherein the consciousness detection system comprises a controller, at least one sensor and an alarm, wherein the controller comprises a processor having circuitry programed to calculate a consciousness score and a memory; wherein the consciousness detection system is configured to periodically conduct at least one response test on the subject to obtain response test results which are used to calculate the consciousness score;

a monitor configured to display data contained within the memory;

an input unit configured to allow a user to manually input data to the device; and a network module configured to allow the device to communicate with a second device for monitoring the relative consciousness of a subject, wherein the response test is an eye movement test conducted with a camera sensor, and the response test results are analyzed by comparison to a machine learning module to quantify the eye movement of the subject and determine the consciousness score, and wherein a loss of consciousness is determined by:
comparing the consciousness score against a predetermined alert range, the predetermined alert range being automatically modified by the machine learning module which is further configured to improve the accuracy of the response test by analyzing the plurality of response test results and associated predetermined alert ranges of a plurality of response tests stored in the memory; and the alarm is triggered by a consciousness score outside the predetermined alert range.

10. The device of claim 9, wherein the controller has further instructions to carry out the periodic conducting, analyzing, and recording repetitively over a time period x and a frequency y.

11. The device of claim 10, wherein the response test comprises:
an eye movement test;
a motor response test; and
a verbal response test.

12. A method for monitoring the relative consciousness of a subject, the method comprising:
conducting at least one response test on the subject to obtain a plurality of response test results, wherein the response test comprises an eye movement test conducted with a camera sensor, and the plurality of response test results are analyzed by comparison to a machine learning module to quantify the eye movement of the subject, wherein the response test is administered by a consciousness detection system, wherein the consciousness detection system comprises a controller, the camera sensor and an alarm, wherein the controller comprises a processor having circuitry programed to calculate a consciousness score and a memory;

recording the response test results in the memory of the processor;

analyzing, with the circuitry of the processor, the response test results to determine a consciousness score;

triggering an alarm based on the consciousness score indicating a loss of consciousness;

analyzing with the machine learning module, the response test results and the consciousness score, to modify the programming of the circuitry such that the accuracy of the method is improved with use; and repeating the at least one response test at predetermined regularly timed intervals, wherein the repetition is initiated by the processor.

13. The method of claim 12, wherein the response test comprises:
an eye movement test;
a motor response test; and
a verbal response test.

14. The method of claim 12, wherein the predetermined regularly timed intervals are dynamically modified by the machine learning module.

15. The method of claim 12, wherein the predetermined alert range is automatically modified by the machine learning module which is further configured to improve the accuracy of the response test by analyzing the plurality of response test results and associated predetermined alert ranges of a plurality of response tests stored in the memory.

* * * * *